United States Patent
Exner et al.

(10) Patent No.: US 7,655,733 B2
(45) Date of Patent: Feb. 2, 2010

(54) POSTCROSSLINKING OF WATER ABSORBING POLYMERS WITH CYCLIC CARBAMATES AND/OR CYCLIC UREAS

(75) Inventors: Kai Michael Exner, Eppelheim (DE); Thomas Daniel, Waldsee (DE); Mark Elliott, Ludwigshafen (DE); Ulrich Riegel, Landstuhl (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 140 days.

(21) Appl. No.: 11/630,949

(22) PCT Filed: Jul. 28, 2005

(86) PCT No.: PCT/EP2005/008198

§ 371 (c)(1),
(2), (4) Date: Dec. 27, 2006

(87) PCT Pub. No.: WO2006/015729

PCT Pub. Date: Feb. 16, 2006

(65) Prior Publication Data

US 2008/0171837 A1    Jul. 17, 2008

(30) Foreign Application Priority Data

Aug. 4, 2004    (DE) .................. 10 2004 038 015

(51) Int. Cl.
C08F 8/30    (2006.01)
C08B 37/00    (2006.01)

(52) U.S. Cl. .................... 525/329.9; 525/54.3

(58) Field of Classification Search ............. 525/54.3, 525/329.9
See application file for complete search history.

(56) References Cited

U.S. PATENT DOCUMENTS

| | | | |
|---|---|---|---|
| 2,399,118 A * | 4/1946 | Homeyer .................... 548/229 |
| 2,437,390 A | 3/1948 | Homeyer |
| 2,755,286 A | 7/1956 | Bell |
| 4,666,983 A | 5/1987 | Tsubakimoto et al. |
| 4,933,462 A | 6/1990 | Dawe et al. |
| 5,019,606 A | 5/1991 | Marten et al. |
| 5,331,059 A | 7/1994 | Engelhardt et al. |
| 5,385,983 A | 1/1995 | Graham |
| 5,840,822 A * | 11/1998 | Lee et al. ..................... 528/44 |
| 5,856,410 A * | 1/1999 | Carrico et al. ............... 525/362 |
| 6,472,478 B1 | 10/2002 | Funk et al. |
| 6,503,979 B1 * | 1/2003 | Funk et al. .................. 524/556 |
| 6,541,577 B2 | 4/2003 | Ohrbom et al. ............. 525/498 |
| 6,559,239 B1 * | 5/2003 | Riegel et al. .............. 525/329.7 |
| 6,657,015 B1 * | 12/2003 | Riegel et al. .............. 525/329.9 |
| 6,699,943 B2 | 3/2004 | Ramesh et al. ............ 525/329.9 |
| 6,720,389 B2 * | 4/2004 | Hatsuda et al. ............ 525/330.1 |
| 7,183,360 B2 * | 2/2007 | Daniel et al. .............. 525/327.6 |
| 7,183,456 B2 * | 2/2007 | Hatsuda et al. ............ 604/372 |
| 7,285,599 B2 * | 10/2007 | Mertens et al. ............. 525/360 |
| 7,378,453 B2 * | 5/2008 | Nogi et al. ..................... 521/53 |
| 7,393,908 B2 * | 7/2008 | Heide et al. ............. 526/318.43 |
| 2002/0061978 A1 * | 5/2002 | Hatsuda et al. .......... 525/330.1 |
| 2002/0165288 A1 * | 11/2002 | Frenz et al. .................... 521/50 |
| 2004/0014901 A1 * | 1/2004 | Heide et al. .............. 525/330.3 |
| 2004/0181031 A1 * | 9/2004 | Nogi et al. ................... 528/480 |
| 2004/0186229 A1 * | 9/2004 | Heide et al. ................. 524/832 |
| 2004/0231065 A1 | 11/2004 | Daniel et al. |
| 2004/0249079 A1 * | 12/2004 | Funk et al. .................. 525/191 |
| 2005/0049379 A1 * | 3/2005 | Adachi et al. ............... 526/319 |
| 2005/0245684 A1 * | 11/2005 | Daniel et al. ................ 525/178 |
| 2005/0245713 A1 * | 11/2005 | Daniel et al. ................ 526/319 |
| 2006/0073969 A1 * | 4/2006 | Torii et al. ................... 502/400 |
| 2006/0204755 A1 * | 9/2006 | Torii et al. ................... 428/402 |
| 2006/0252900 A1 * | 11/2006 | Bowman et al. ............. 526/318 |
| 2007/0065503 A1 * | 3/2007 | Harren et al. ................ 424/455 |
| 2007/0161759 A1 * | 7/2007 | Riegel et al. ................. 525/375 |
| 2007/0244283 A1 * | 10/2007 | Riegel et al. ................. 526/318 |
| 2007/0293632 A1 * | 12/2007 | Riegel et al. .............. 525/329.9 |
| 2008/0125533 A1 * | 5/2008 | Riegel et al. ................. 524/417 |
| 2008/0161522 A1 * | 7/2008 | Riegel et al. .............. 526/317.1 |

FOREIGN PATENT DOCUMENTS

| | | |
|---|---|---|
| DE | 198 07 992 C1 | 7/1999 |
| DE | 198 07 502 A1 | 9/1999 |
| DE | 198 54 573 A1 | 5/2000 |
| DE | 102 04 937 | 8/2003 |
| DE | 10204937 A1 * | 8/2003 |
| EP | 0 083 022 A2 | 7/1983 |
| EP | 0 349 935 | 1/1990 |

(Continued)

OTHER PUBLICATIONS

Machine translation of DE 10204937 A1 (2008).*

(Continued)

*Primary Examiner*—Mark Eashoo
*Assistant Examiner*—Liam J Heincer
(74) *Attorney, Agent, or Firm*—Marshall, Gerstein & Borun LLP

(57) ABSTRACT

Disclosed is a process for postcrosslinking a water absorbing polymer by the polymer being treated with at least one postcrosslinker and postcrosslinked and dried during or after the treatment by raising the temperature, the at least one postcrosslinker being a cyclic carbamate or a cyclic urea, wherein the cyclic carbamate or the cyclic urea was obtained by reacting respectively an aminoalcohol or a diamine with a cyclic carbonate.

6 Claims, No Drawings

FOREIGN PATENT DOCUMENTS

| | | |
|---|---|---|
| EP | 0 530 438 A1 | 3/1993 |
| EP | 0 543 303 A1 | 5/1993 |
| EP | 0 900 825 | 3/1999 |
| JP | 60-097967 | 5/1985 |
| JP | 60-152476 | 8/1985 |
| JP | 61-007260 | 1/1986 |
| JP | 2002/105064 | 4/2002 |
| WO | WO-03/031482 | 4/2003 |

OTHER PUBLICATIONS

International Search Report in PCT/EP2005/008198 in Apr. 10, 2006.

Ishikawa et al., Nippon Kagaku Kaishi, No. 8, pp. 1592-1594 (1974).

Kooh et al., Tetrahedron Letters, No. 34, pp. 2899-2900 (1974).

Kutner, Tetrahedron Letters, No. 26, pp. 3495-3498 (1961).

* cited by examiner

US 7,655,733 B2

POSTCROSSLINKING OF WATER ABSORBING POLYMERS WITH CYCLIC CARBAMATES AND/OR CYCLIC UREAS

CROSS-REFERENCE TO RELATED APPLICATIONS

This is the U.S. national phase application of International Application No. PCT/EP2005/008198, filed Jul. 28, 2005, which claims the benefit of German patent application No. 10 2004 038 015.5, filed Aug. 4, 2004.

DESCRIPTION

The present invention relates to a process for postcrosslinking water absorbing polymers with cyclic carbamates and/or cyclic ureas.

Water absorbing polymers are in particular polymers of (co)polymerized hydrophilic monomers, graft (co)polymers of one or more hydrophilic monomers on a suitable grafting base, crosslinked ethers of cellulose or of starch, crosslinked carboxymethylcellulose, partially crosslinked polyalkylene oxide or natural products that are swellable in aqueous fluids, such as guar derivatives for example. Such hydrogels are used as products capable of absorbing aqueous solutions to manufacture diapers, tampons, sanitary napkins and other hygiene articles, but also as water retaining agents in market gardening.

To improve their performance characteristics, such as saline flow conductivity (SFC) in the diaper and absorbency under load (AUL), water absorbing polymers are generally surface or gel postcrosslinked. This postcrosslinking is preferably effected in the aqueous gel phase or as postcrosslinking of the ground and classified polymeric particles.

Useful crosslinkers for this purpose are compounds which comprise at least two groups capable of forming covalent bonds with the carboxylate groups of the hydrophilic polymer. Examples of suitable compounds are di- or polyglycidyl compounds, such as diglycidyl phosphonates, alkoxysilyl compounds, polyaziridines, polyamines or polyamidoamines, and the identified compounds can also be used in mixtures with each other (see for example EP-A-0 083 022, EP-A-0 543303 and EP-A-0 530 438). Polyamidoamines useful as crosslinkers are described in particular in EP-A-0 349 935.

One significant disadvantage of these crosslinkers is their high reactivity, since it requires that special precautions be taken in the manufacturing operation in order that unwanted secondary effects may be avoided. Similarly, the aforementioned crosslinkers have skin irritating properties, which appears to be problematical for the use in hygiene articles.

Known crosslinkers include polyfunctional alcohols. For instance, U.S. Pat. Nos. 4,666,983 and 5,385,983 teach the use of hydrophilic polyalcohols and the use of polyhydroxy surfactants respectively. The reaction in these references is carried out at high temperatures in the range from 120 to 250° C. The process has the disadvantage that the esterification reaction which leads to crosslinking is very slow even at these temperatures.

Furthermore, compounds described as suitable crosslinkers include 2-oxazolidinone and its derivatives in DE-A-198 07 502, 2,3-morpholinedione and its derivatives in WO-A-03/031482, 2-oxotetrahydro-1,3-oxazine and its derivatives in DE-A-198 54 573, N-acyloxazolidin-2-ones in DE-A-198 54 574 and bis- and polyoxazolidin-2-ones in DE-A-198 07 992. True, these compounds do meet the requirements with regard to use in hygiene articles, but are not commercially available and are relatively difficult to prepare pure.

For instance, it is stated in Tetrahedron Letters, 1974, pages 2899 to 2900, that N-(2-hydroxyethyl)oxazolidin-2-one is obtainable by oxidative carbonylation of diethanolamine in the presence of elemental selenium. Such a material is not suitable for use in the hygiene sector because of the toxicity of selenium. Journal of Organic Chemistry, 1961, pages 3495 to 3498, teaches that diethanolamine can be converted into N-(2-hydroxyethyl)oxazolidin-2-one with a 92% yield by reaction with ethyl trichloroacetate. This process is not economical because of the costs of material and the coproduction of chloroform.

U.S. Pat. No. 2,437,390 discloses the preparation of 2-oxazolidinones by reaction of ethanolamines with dialkyl carbonates. The dialkyl carbonates are used in excess. The alcohol freed is preferably distilled off continuously. The 2-oxazolidinones are distilled or recrystallized. The disadvantage with this process is the use of the costly dialkyl carbonates. U.S. Pat. No. 4,933,462 describes the use of dimethyl carbonate on the lines of U.S. Pat. No. 2,437,390.

EP-A-0 900 825 describes the use of 2-oxazolidinone as a crosslinker, the 2-oxazolidinone having been prepared by reacting ethanolamine with potassium cyanate.

U.S. Pat. No. 2,755,286 teaches the preparation of 2-oxazolidinones by cyclizing transesterification of hydroxyalkyl N-(hydroxyalkyl)carbamates. The reaction products are continuously distilled off and the 2-oxazolidinones crystallize in the distillate. The distillation of 2-oxazolidinones requires inconvenient distillations at pressures of 1 to 1.2 Torr, which are very costly to achieve under industrial conditions. Distillations at higher pressures, associated with higher temperatures, lead to polymeric products, as described in Nippon Kagaku Kaishi, 1974, volume 8, pages 1592 to 1594. The hydroxyalkyl N-(hydroxyalkyl)carbamates are obtainable by reaction of 2-hydroxyalkylamines with cyclic carbonates.

JP-61-007260 discloses the preparation of 2-oxazolidinones by reaction of ethanolamines with cyclic carbonates at reduced pressure, the resulting glycol being removable by distillation.

JP-60-097967 and JP-60-152476 describe the reaction of ethanolamines with cyclic carbonates wherein the reaction products are purified using acidic ion exchange resins.

JP-2002-105064 describes the reaction of dialkyl carbonates with ethanolamines in the presence of alkali metal alkoxides.

The present invention has for its object to provide a process for postcrosslinking water absorbent polymers which utilizes postcrosslinkers which are generally recognized as safe by occupational hygienists but at the same time have sufficient reactivity and also are simple to synthesize. More particularly, the postcrosslinkers shall have an as-synthesized form such that there is no need to purify crude products, as for example by distillation or crystallization of the postcrosslinkers.

The present invention further has for its object to provide a postcrosslinker mixture which has high stability in storage.

The postcrosslinkers must not lead to discolorations or odors in the end product, as for example through side or secondary products.

We have found that this object is achieved by providing a process for postcrosslinking a water absorbing polymer by the polymer being treated with at least one postcrosslinker, the at least one postcrosslinker being a cyclic carbamate or a cyclic urea, wherein the cyclic carbamate or the cyclic urea was obtained by reacting respectively an aminoalcohol or a diamine with a cyclic carbonate.

Preferably, the water absorbing polymers are postcrosslinked and/or dried during or after the treatment with the at least one postcrosslinker by raising the temperature.

More preferably, the water absorbing polymers are dried and postcrosslinked during or after the treatment with the at least one postcrosslinker by raising the temperature.

Preference is given to using cyclic carbamates. Useful cyclic carbamates include for example compounds of the general formula I

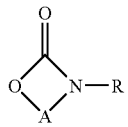

where
R are hydrogen, $C_1$-$C_{12}$-alkyl, $C_2$-$C_{12}$-alkenyl, $C_2$-$C_{12}$-acyl or $C_2$-$C_{12}$-hydroxyalkyl, with $C_3$-$C_{12}$-alkyl, $C_3$-$C_{12}$-alkenyl, $C_3$-$C_{12}$-acyl or $C_3$-$C_{12}$-hydroxyalkyl being branched or unbranched and $C_1$-$C_{12}$-alkyl, $C_2$-$C_{12}$-alkenyl, $C_2$-$C_{12}$-acyl or $C_2$-$C_{12}$-hydroxyalkyl being halogen substituted or not, halogen being fluorine, chlorine, bromine and/or iodine, and
A is $C_2$-$C_{12}$-alkylene, with $C_3$-$C_{12}$-alkylene being branched or unbranched and $C_2$-$C_{12}$-alkylene being halogen substituted or not, halogen being fluorine, chlorine, bromine and/or iodine.

Examples of R radicals are hydrogen, methyl, ethyl, propyl, prop-2-yl(isopropyl), butyl, but-2-yl(isobutyl), pentyl, pent-2-yl, pent-3-yl, 2-methylpentyl, 3-methylpentyl, 3-methylpent-2-yl, 2,2-dimethylpropyl, trifluoromethyl, ethenyl, propen-2-yl, buten-2-yl, acetyl, 2-hydroxyethyl, 2-hydroxypropyl, 3-hydroxypropyl, 2-hydroxybutyl, 3-hydroxybutyl, 4-hydroxybutyl, 2-hydroxy-2-methylpropyl and 3-hydroxy-2-methylpropyl.

Examples of A radicals are

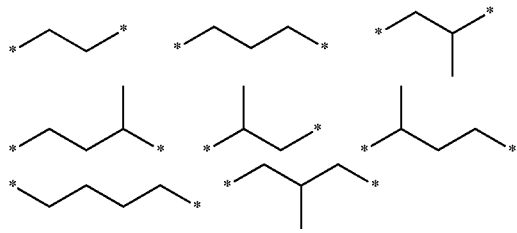

where * indicates the positions of attachment.

Preference is given to cyclic carbamates of the general formula I where R are hydrogen, $C_1$-$C_6$-alkyl, $C_2$-$C_6$-alkenyl, $C_2$-$C_6$-acyl or $C_2$-$C_6$-hydroxyalkyl, with $C_3$-$C_6$-alkyl, $C_3$-$C_6$-alkenyl, $C_3$-$C_6$-acyl or $C_3$-$C_6$-hydroxyalkyl being branched or unbranched and $C_1$-$C_6$-alkyl, $C_2$-$C_6$-alkenyl, $C_2$-$C_6$-acyl or $C_2$-$C_6$-hydroxyalkyl being halogen substituted or not, halogen being fluorine, chlorine, bromine and/or iodine, and A is $C_2$-$C_6$-alkylene, with $C_3$-$C_6$-alkylene being branched or unbranched and $C_2$-$C_6$-alkylene being halogen substituted or not, halogen being fluorine, chlorine, bromine and/or iodine.

Particular preference is given to cyclic carbamates of the general formula I where R are hydrogen or $C_2$-$C_6$-hydroxyalkyl with $C_3$-$C_6$-hydroxyalkyl being branched or unbranched, and A is $C_2$-$C_6$-alkylene, with $C_3$-$C_6$-alkylene being branched or unbranched.

Very particular preference is given to cyclic carbamates of the general formula I where R are hydrogen or $C_2$-$C_3$-hydroxyalkyl, with $C_3$-hydroxyalkyl being branched or unbranched, and A is $C_2$-$C_3$-alkylene, with $C_3$-alkylene being branched or unbranched.

2-Hydroxyethyl, 2-hydroxypropyl and 3-hydroxypropyl are very particularly preferred R radicals.

The compound of the general formula I is preferably a five- or six-membered ring.

2-Oxazolidinone, 2-hydroxyethyloxazolidin-2-one, 3-hydroxyethyloxazolidin-2-one, 2-hydroxypropyloxazolidin-2-one and 2-oxotetrahydro-1,3-oxazine are preferred cyclic carbamates.

The cyclic carbamates are prepared by thermal reaction of an aminoalcohol with a cyclic carbonate. Useful cyclic carbonates include for example 1,3-dioxolan-2-one, 4-methyl-1,3-dioxolan-2-one, 4,5-dimethyl-1,3-dioxolan-2-one, 4,4-dimethyl-1,3-dioxolan-2-one, 4-ethyl-1,3-dioxolan-2-one, 4-hydroxymethyl-1,3-dioxolan-2-one, 1,3-dioxan-2-one, 4-methyl-1,3-dioxan-2-one, 5-methyl-1,3-dioxan-2-one, 5,5-dimethyl-1,3-dioxan-2-one, 4,6-dimethyl-1,3-dioxan-2-one and 1,3-dioxepan-2-one. Useful aminoalcohols include for example ethanolamine, diethanolamine and N-hydroxyethylpropanolamine. The reaction temperature is typically in the range from 80 to 200° C., preferably in the range from 100 to 150° C. and more preferably in the range from 110 to 130° C. The reaction can be carried out at underpressure, overpressure or atmospheric pressure, the last being preferred. Preferably, the diol freed from the cyclic carbonate in the course of the reaction is not distilled off during the reaction.

The reaction can of course be hastened by the diol freed in the course of the reaction being distilled off continuously, preferably at a pressure corresponding to the desired reaction temperature.

It is advantageous to use basic catalysts, examples being sodium hydroxide, potassium hydroxide, sodium ethoxide, sodium carbonate and potassium carbonate. This ensures sufficiently high reaction rates even at comparatively low reaction temperatures, and minimizes product discolorations. When basic catalysts are used, the reaction temperature is typically in the range from 60 to 180° C., preferably in the range from 70 to 140° C. and more preferably in the range from 90 to 110° C.

Dialkanolamines, in which the alkanol groups may be the same or different, react almost quantitatively and therefore are preferred for use as a starting material. Useful dialkanolamines include N,N-di(2-ethanol)amine, N,N-di(2-propanol)amine, N,N-di(3-propanol)amine, N,N-di(2-butanol)amine, N,N-di(3-butanol)amine, N-ethanol-N-(2-propanol)amine, N-(2-ethanol)-N-(2-butanol)amine and N-(2-propanol)-N-(2-butanol)amine. N,N-Di(2-ethanol)amine or diethanolamine is preferred.

The as-synthesized crude product is colorless and does not comprise any odorous side or secondary products and therefore can be used directly for postcrosslinking.

When the diol freed from the cyclic carbonate in the course of the reaction is a glycol (a vicinal diol), it is preferable for the diol to be distilled off to a substantial degree, i.e., to not less than 70%, preferably not less than 80% and more preferably not less than 90%, after the reaction has ended.

When the diol freed from the cyclic carbonate in the course of the reaction is an n,m diol where m>n and m−n>1, it is preferable for the diol not to be distilled off to any substantial degree, i.e., to not more than 40%, preferably not more than 20% and more preferably not more than 10%, after the reaction has ended.

The cyclic carbamate is typically not further purified, i.e., not distilled or recrystallized, especially when the by-produced diol neither hinders postcrosslinking nor leads to odor problems.

Cyclicureas may be prepared and used similarly to the cyclic carbamates.

The cyclic carbamate is preferably used in the form of a solution in an inert solvent. A preferred inert solvent is water or a mixture of water with an alcohol. However, it is possible to use any organic solvent which is miscible with water in any proportion and which itself is not reactive under the process conditions. When an alcohol-water mixture is used, the alcohol content of this solution is for example in the range from 10% to 90% by weight, preferably in the range from 15% to 70% by weight and especially in the range from 20% to 60% by weight. Any alcohols miscible with water in any proportion can be used as can mixtures of plural alcohols (for example methanol+isopropanol+water). Alcohol mixtures may comprise the alcohols in any desired mixing ratio. However, it is particularly preferable to use the following alcohols in aqueous solution: methanol, ethanol, n-propanol, polyethylene glycols having up to 20 EO units, propane-1,3-diol, 2-methylpropane-1,3-diol, 2,2-dimethylpropane-1,3-diol, butane-1,4-diol and more preferably isopropanol.

It will be appreciated that the postcrosslinker can be used as a nonaqueous solution. In this case, the dried hydrogel is moistened with water before, during or after being sprayed with the postcrosslinker solution.

The process of the present invention can utilize the cyclic carbamates alone or combined with other postcrosslinkers, for example ethylene glycol diglycidyl ether, diethylene glycol diglycidyl ether, polyethylene glycol diglycidyl ether, propylene glycol diglycidyl ether, dipropylene glycol diglycidyl ether, polypropylene glycol diglycidyl ether, glycerol diglycidyl ether, polyglycerol diglycidyl ether, epichlorohydrin, etylenediamine, ethylene glycol, diethylene glycol, triethylene glycol, polyethylene glycol, propylene glycol, dipropylene glycol, tripropylene glycol, polypropylene glycol, butylene glycol, 1,3-propanediol, 1,4-butanediol, bisphenol A, glycerol, trimethylolpropane, pentaerythritol, sorbitol, diethanolamine, triethanolamine, etylenediamine.

It may be preferable for salts of polyvalent cations to be additionally used in postcrosslinking. Examples of polyvalent cations are bivalent cations, such as the cations of zinc, magnesium, calcium, barium and strontium, tervalent cations, such as the cations of aluminum, iron, chromium, rare earths and manganese, tetravalent cations, such as the cations of titanium and zirconium. Possible counter-ions include chloride, bromide, sulfate, bisulfate, carbonate, bicarbonate, nitrate, phosphate, hydrogenphosphate, dihydrogenphosphate and carboxylate, such as acetate and lactate. Aluminum sulfate is preferred. Preference is further given to dispersions of calcium phosphate, calcium sulfate and barium sulfate.

A preferred embodiment utilizes the cyclic carbamate together with a diol. Useful diols include $C_2$-$C_{12}$-diols, with $C_3$-$C_{12}$-diols being branched or unbranched. Advantageously, the diol freed from the cyclic carbamate in the course of the preparation of the cyclic carbamate remains at least partly in the crude product, which can then be preferably used directly, without further purification.

Preferred diols include $C_2$-$C_6$-diols, with $C_3$-$C_6$-diols being branched or unbranched.

Very particular preference is given to diols which are not glycols (vicinal diols), such as propane-1,3-diol, butane-1,3-diol, 2-methylpropane-1,3-diol 2,2-dimethylpropane-1,3-diol and butane-1,4-diol.

Glycols under postcrosslinking conditions are converted at least to some extent into odorous products and that, for example, propylene glycol gives rise at 160° C. to acetone, which is freed upon moistening of the superabsorbent and leads to unpleasant odors.

A particularly preferred embodiment utilizes the cyclic carbamate together with an organic carbonate, preferably a cyclic carbonate. Useful cyclic carbonates include for example 1,3-dioxolan-2-one, 4-methyl-1,3-dioxolan-2-one, 4,5-dimethyl-1,3-dioxolan-2-one, 4,4-dimethyl-1,3-dioxolan-2-one, 4-ethyl-1,3-dioxolan-2-one, 4-hydroxymethyl-1, 3-dioxolan-2-one, 1,3-dioxan-2-one, 4-methyl-1,3-dioxan-2-one, 5-methyl-1,3-dioxan-2-one, 5,5-dimethyl-1,3-dioxan-2-one, 4,6-dimethyl-1,3-dioxan-2-one and 1,3-dioxepan-2-one. Advantageously, the cyclic carbamate is prepared using an excess of cyclic carbonate, which then remains in the crude product at least to some extent, preferably almost fully. Almost fully is to be understood as meaning that the crude product's cyclic carbonate content is lowered only to that extent which is inevitable if not less than 70%, preferably not less than 80% and more preferably not less than 90% of the diol freed in the course of the preparation of the cyclic carbamate is to be distilled off. Some cyclic carbonate is carried out as entrainment in the course of diol distillation.

The postcrosslinking solution is preferably sprayed onto the polymer in suitable spray mixers. Following spraying, the polymer powder is thermally dried, and the crosslinking reaction can take place not only before but also during drying. Preference is given to spray application of a solution of the crosslinker in reaction mixers or mixing and drying systems such as for example Lodige mixers, BEPEX® mixers, NAUTA® mixers, SCHUGGI® mixers or PROCESSALL®. Moreover, fluidized bed dryers can also be used. The postcrosslinking and drying temperature range preferably extends from 30 to 210° C., especially from 80 to 195° C. and more preferably from 120 to 185° C.

Drying can take place in the mixer itself, by heating the outer casing or by blowing hot air into the mixer. It is similarly possible to use a downstream dryer such as a tray dryer, a rotary tube oven or a heatable screw. But it is also possible, for example, to use an azeotropic distillation as a drying process. The preferred residence time at this temperature in the reaction mixer or dryer is less than 120 minutes, more preferably less than 90 minutes and most preferably less than 60 minutes.

The cyclic carbamate is used therein in an amount from 0.01% to 5% by weight, preferably from 0.01% to 1.0% by weight and more preferably from 0.05% to 0.5% by weight, based on the polymer used.

The polyvalent cation is used in an amount from 0% to 0.5% by weight, preferably from 0.005% to 0.1% by weight and more preferably from 0.03% to 0.08% by weight, based on the polymer used.

When the cyclic carbamate is used together with the diol, the molar ratio of diol to carbamate is typically in the range from 1:50 to 2:1, preferably in the range from 1:10 to 1.5:1 and more preferably in the range from 1:2.5 to 1.1:1.

When the cyclic carbamate is used together with an organic carbonate, the molar ratio of carbamate to carbonate is typically in the range from 1000:1 to 2:1, preferably in the range from 200:1 to 5:1 and more preferably in the range from 40:1 to 10:1.

A very particularly preferred embodiment utilizes a post-crosslinker solution, i.e., the postcrosslinker solution, as well as the cyclic carbamate, comprises all further components, such as solvent, further postcrosslinkers, polyvalent cations, diol, surfactants, such as sorbitan monolaurate, dispersible inorganic powders, such as pyrogenic silica and calcium phosphate, and/or organic carbonates.

Organic carbonates enhance in particular the stability of the postcrosslinker solution in storage.

A further preferred embodiment of the invention utilizes the postcrosslinker solution in a ratio from 0.5% to 20% by weight, based on the mass of the polymer. A solution quantity from 1% to 10% by weight, based on the polymer, is particularly preferred.

The water absorbing polymers to be used in the process of the present invention are in particular polymers of crosslinked (co)polymerized hydrophilic monomers, polyaspartic acid, graft (co)polymers of one or more hydrophilic monomers on a suitable grafting base, crosslinked cellulose ethers, crosslinked starch ethers or natural products which are swellable in aqueous fluids, such as guar derivatives for example. Preferably the polymer to be crosslinked is a polymer which contains structural units which are derived from acrylic acid or acrylic esters or which were obtained by graft copolymerization of acrylic acid or acrylic esters onto a water-soluble polymeric matrix. These hydrogels are known to one skilled in the art and are described for example in U.S. Pat. No. 4,286,082, DE-C-27 06 135, U.S. Pat. No. 4,340, 706, DE-C-37 13 601, DE-C-28 40 010, DE-A43 44 548, DE-A40 20 780, DE-A-40 15 085, DE-A-39 17 846, DE-A-38 07 289, DE-A-35 33 337, DE-A-35 03 458, DE-A42 44 548, DE-A42 19 607, DE-A40 21 847, DE-A-38 31 261, DE-A-35 11 086, DE-A-31 18 172, DE-A-30 28 043, DE-A44 18 881, EP-A-0 801 483, EP-A-0 455 985, EP-A-0 467 073, EP-A-0 312 952, EP-A-0 205 874, EP-A-0 499 774, DE-A 26 12 846, DE-A40 20 780, EP-A-0 205 674, U.S. Pat. No. 5,145,906, EP-A-0 530 438, EP-A-0 670 073, U.S. Pat. Nos. 4,057,521, 4,062,817, 4,525,527, 4,295,987, 5,011,892, 4,076,663 or 4,931,497.

Examples of hydrophilic monomers useful for preparing these water absorbing polymers are polymerization-capable acids, such as acrylic acid, methacrylic acid, vinylsulfonic acid, vinylphosphonic acid, maleic acid including its anhydride, fumaric acid, itaconic acid, 2-acrylamido-2-methyl-propanesulfonic acid, 2-acrylamido-2-methylpropanephos-phonic acid and also their amides, hydroxyalkyl esters and amino- or ammonio-containing esters and amides and also the alkali metal and/or ammonium salts of the acid-functional monomers. Also suitable are water-soluble N-vinylamides such as N-vinylformamide or else diallyidimethylammonium chloride.

Preferred hydrophilic monomers are compounds of the general formula II

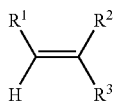

(II)

where
R$^1$ is hydrogen, methyl, ethyl or carboxyl,
R$^2$ is —COOR$^4$, hydroxysulfonyl or phosphonyl, a C$_1$-C$_4$-alkanol-esterified phosphonyl group or a group of the formula III

(III)

R$^3$ is hydrogen, methyl or ethyl,
R$^4$ is hydrogen, C$_1$-C$_4$-aminoalkyl, C$_1$-C$_4$-hydroxyalkyl, alkali metal ion or ammonium ion, and
R$^5$ is a sulfonyl group, a phosphonyl group or a carboxyl group or an alkali metal or ammonium salt of each of these.
Examples of C$_1$-C$_4$-alkanols are methanol, ethanol, n-propanol, isopropanol or n-butanol.

Particularly preferred hydrophilic monomers are acrylic acid and methacrylic acid and also their alkali metal or ammonium salts, for example sodium acrylate, potassium acrylate or ammonium acrylate.

Suitable grafting bases for water absorbing polymers obtainable via graft copolymerization of olefinically unsaturated acids or their alkali metal or ammonium salts may be of natural or synthetic origin. Examples are starch, cellulose or cellulose derivatives and also other polysaccharides and oligosaccharides, polyalkylene oxides, in particular polyethylene oxides and polypropylene oxides, and also hydrophilic polyesters.

Suitable polyalkylene oxides have for example the formula IV

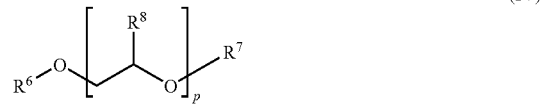

(IV)

where
R$^6$ and R$^7$ are each independently hydrogen, alkyl, alkenyl or aryl,
R$^8$ is hydrogen or methyl, and
p is an integer from 1 to 500.
R$^6$ and R$^7$ are each preferably hydrogen, C$_1$-C$_4$-alkyl, C$_2$-C$_6$-alkenyl or phenyl.

Preferred water absorbing polymers are in particular polyacrylates, polymethacrylates and also the graft polymers described in U.S. Pat. Nos. 4,931,497, 5,011,892 and 5,041, 496.

The water absorbing polymers are preferably in crosslinked form; that is, they include compounds having at least two double bonds which have been copolymerized into the polymer network. Suitable crosslinkers are in particular N,N'-methylenebisacrylamide and N,N'-methylenebis-methacrylamide, esters of unsaturated mono- or polycar-boxylic acids of polyols, such as diacrylate or triacrylate, examples being the diacrylates and dimethacrylates of butanediol and ethylene glycol and also trimethylolpropane triacrylate and allyl compounds such as allyl(meth)acrylate, triallyl cyanurate, diallyl maleate, polyallyl esters, tetraallyloxyethane, triallylamine, tetraallylethylenediamine, allyl esters of phosphoric acid and also vinylphosphonic acid derivatives as described for example in EP-A-0 343 427. The process of the present invention may also utilize dimethacrylates of polyethylene glycols, the polyethylene glycols used having a molecular weight between 300 and 1000. Di- and/or trimethacrylates of multiply ethoxylated trimethylolpropane or trimethylolethane are also useful. Trimethacrylates of 5 tuply to 30 tuply ethoxylated trimethylolpropane or trimethylolethane are particularly useful. Trimethacrylates of 10 tuply to 20 tuply ethoxylated trimethylolpropane or trimethylolethane are even more useful. The triacrylates of 13 tuply to 18 tuply ethoxylated trimethylolpropane or trimethylolethane are most useful.

The process of the present invention may further utilize hydrogels prepared using polyallyl ethers as crosslinkers and by acidic homopolymerization of acrylic acid. Useful crosslinkers include pentaerythritol triallyl ether, pentaerythritol tetraallyl ether, polyethylene glycol diallyl ether, monoethylene glycol diallyl ether, glycerol diallyl ether, glycerol triallyl ether, polyallyl ethers based on sorbitol and also ethoxylated versions thereof.

Crosslinkers which are very particularly preferred are the di- or tri(meth)acrylated multiply ethoxylated and/or propoxylated glycerols as described for example in prior German patent application 103 19 462.2. Di- and/or trimethacrylates of 3 to 10 tuply ethoxylated glycerol are particularly advantageous. Di- or trimethacrylates of 1 to 5 tuply ethoxylated and/or propoxylated glycerol are very particularly preferred. The trimethacrylates of 3 to 5 tuply ethoxylated or propoxylated glycerol are most preferred.

The preferred methods of making the base polymer which can be used in the process of the present invention are described in "Modern Superabsorbent Polymer Technology", F. L. Buchholz and A. T. Graham, Wiley-VCH, 1998, pages 77 to 84. Particular preference is given to base polymers which are produced in a kneader as described for example in WO-A-01/38402 or on a belt reactor as described for example in EP-A-0 955 086.

The water absorbing polymer is preferably a polymeric acrylic acid or a polyacrylate. This water absorbing polymer may be prepared according to a literature method. Preference is given to polymers which contain crosslinking comonomers in amounts from 0.001 to 10 mol % and preferably from 0.01 to 1 mol %, but most preference is given to polymers which were obtained by free-radical polymerization using a polyfunctional ethylenically unsaturated free-radical crosslinker which additionally bears at least one free hydroxyl group (such as for example pentaerythritol triallyl ether or trimethylolpropane diallyl ether).

The water absorbing polymers are preparable by conventional polymerization processes. Preference is given to addition polymerization in aqueous solution by the process known as gel polymerization. In this process from 15 to 50% by weight aqueous solutions of one or more hydrophilic monomers and if appropriate of a suitable grafting base are polymerized in the presence of a free-radical initiator, preferably without mechanical mixing, by utilizing the Trommsdorff-Norrish effect (Makromol. Chem. 1, 169 (1947)). The addition polymerization reaction may be carried out in the temperature range between 0 and 150° C. and preferably between 10 and 100° C., not only at atmospheric pressure but also at elevated or reduced pressure. As customary, the addition polymerization may also be carried out in a protective gas atmosphere, preferably under nitrogen. The addition polymerization may be initiated using high-energy electromagnetic radiation or the customary chemical addition polymerization initiators, for example organic peroxides, such as benzoyl peroxide, tert-butyl hydroperoxide, methyl ethyl ketone peroxide, cumene hydroperoxide, azo compounds such as azodiisobutyronitrile and also inorganic peroxo compounds such as $(NH_4)_2S_2O_8$, $K_2S_2O_8$ or $H_2O_2$. They may if appropriate be used in combination with reducing agents such as sodium bisulfite and iron(II) sulfate or redox systems where the reducing component is an aliphatic and aromatic sulfinic acid, such as benzenesulfinic acid and toluenesulfinic acid or derivatives thereof, such as Mannich adducts of sulfinic acids, aldehydes and amino compounds as described in DE-A-13 01 566. The performance properties of the polymers may be further improved by postheating the polymer gels for a number of hours in the temperature range from 50 to 130° C. and preferably from 70 to 100° C.

The gels obtained are neutralized, for example to 0-100 mol %, preferably 25-100 mol % and very preferably to 50-85 mol %, based on monomer used, for which the customary neutralizing agents can be used, preferably alkali metal hydroxides or oxides, but very preferably sodium hydroxide, sodium carbonate and sodium bicarbonate.

Neutralization is customarily effected by admixing the neutralizing agent as an aqueous solution or else preferably as a solid. For this purpose, the gel is mechanically comminuted, by means of a meat grinder for example, and the neutralizing agent is sprayed on, scattered over or poured on and then carefully mixed in. To effect homogenization, the resultant gel mass may be passed through the meat grinder again a number of times. The neutralized gel mass is then dried using a belt or drum dryer until the residual moisture content is preferably below 10% by weight and especially below 5% by weight. The dried hydrogel is subsequently ground and sieved, the customary grinding apparatus being roll mills, pin mills or swing mills. The particle size of the sieved polymer is preferably in the range from 45 to 1000 μm, more preferably in the range from 45 to 850 μm, even more preferably in the range from 100 to 800 μm and yet more preferably in the range from 100 to 700 μm. Preference is further given to hydrogels where not less than 97% by weight of the particles have a diameter between 150 to 600 μm. Particular preference is given to hydrogels where not less than 97% by weight of the particles have a diameter between 150 to 600 μm and where the fraction of particles having a diameter between 500 to 600 μm is not more than 10% by weight.

The present invention further provides a process for producing hygiene articles, preferably diapers, comprising the postcrosslinking water absorbing polymer by the polymer being treated with at least one postcrosslinker, the at least one postcrosslinker being a cyclic carbamate or a cyclic urea, wherein the cyclic carbamate or the cyclic urea was obtained by reacting respectively an aminoalcohol or a diamine with a cyclic carbonate.

The present invention further provides mixtures A comprising an n,m diol where m>n and m−n>1 and a cyclic carbamate in a molar ratio of n,m diol to carbamate in the range from 1.1:1 to 1:2.5, their production by the process described above and also their use for postcrosslinking water absorbing polymers.

The present invention further provides mixtures B comprising a diol, a cyclic carbamate and a cyclic carbonate, the cyclic carbamate having a hydroxyalkyl group on the nitrogen atom and the molar ratio of carbamate to carbonate being in the range from 1000:1 to 5:1, preferably in the range from 200:1 to 5:1 and more preferably in the range from 40:1 to 10:1, their production by the process described above and also their use for postcrosslinking water absorbing polymers.

The two abovementioned mixtures according to the present invention comprise a solvent, preferably in an amount from 50% to 99% by weight, preferably from 60% to 98% by weight and more preferably from 70% to 97% by weight. Water is a preferred solvent.

The mixtures A and/or B comprise a polyvalent cation, preferably in an amount from 0% to 5% by weight, preferably from 0.01% to 2% by weight and more preferably from 0.1 to 1.0% by weight. $Al^{3+}$ is a preferred polyvalent cation.

The mixtures A and/or B comprise at least one surfactant, preferably in an amount from 0% to 4% by weight, preferably from 0.01% to 2% by weight and more preferably from 0.1% to 1% by weight. Sorbitan monolaurate is a preferred surfactant.

The mixtures A and/or B comprise at least one monohydric alcohol, preferably in an amount from 0% to 60% by weight, preferably from 0% to 40% by weight and more preferably from 20% to 40% by weight. Isopropanol is a preferred alcohol.

The present invention further provides for the production of the mixtures A and B, their use for postcrosslinking water absorbing polymers and also the postcrosslinked polymers thus obtainable.

The CRC value [g/g] of the postcrosslinked water absorbing polymers according to the present invention can be measured by the methods indicated in the description part and is preferably more than 15, especially more than 20, more preferably more than 25, especially more than 30 and even more preferably more than 35.

The AUL 0.7 psi value [g/g] of the postcrosslinked water absorbing polymers according to the present invention can be measured by the methods indicated in the description part and is preferably more than 10, especially more than 15, more preferably more than 20, especially more than 25 and even more preferably more than 30.

The extractables content [% by weight] of the postcrosslinked water absorbing polymers according to the present invention can be measured by the methods indicated in the description part and is preferably less than 15, especially less than 12, more preferably less than 10, especially less than 8 and even more preferably less than 7.

The level of unconverted ethylenically unsaturated monomers [weight ppm] of the postcrosslinked water absorbing polymers according to the present invention can be measured by the methods indicated in the description part and is preferably less than 500, especially less than 400, more preferably less than 300, especially less than 200 and even more preferably less than 100.

The present invention further provides for the use of postcrosslinked polymers postcrosslinked with mixtures A or B in hygiene articles and packaging materials, especially diapers, and also the hygiene articles themselves. For example, the hygiene article can be constructed as follows:
(A) a liquid pervious topsheet
(B) a liquid impervious backsheet
(C) a core which is situated between (A) and (B) and comprises
　from 10% to 100% by weight of the crosslinked swellable hydrogel forming polymer according to the present invention
　from 0% to 90% by weight of hydrophilic fiber material
　　preferably from 30% to 100% by weight of the crosslinked swellable hydrogel forming polymer according to the present invention, from 0% to 70% by weight of hydrophilic fiber material
　　more preferably from 50% to 100% by weight of the crosslinked swellable hydrogel forming polymer according to the present invention, from 0% to 50% by weight of hydrophilic fiber material
　　even more preferably from 70% to 100% by weight of the crosslinked swellable hydrogel forming polymer according to the present invention, from 0% to 30% by weight of hydrophilic fiber material
　　most preferably from 90% to 100% by weight of the crosslinked swellable hydrogel forming polymer according to the present invention, from 0% to 10% by weight of hydrophilic fiber material
(D) if appropriate, a tissue layer situated directly above and below the core (C) and
(E) if appropriate, an acquisition layer situated between (A) and (C).

Hygiene articles for the purposes of the present invention include for example incontinence pads and incontinence briefs for adults or diapers for babies.

The liquid pervious topsheet (A) is the layer which is in direct contact with the skin. Its material consists of customary synthetic or manufactured natural-polymer fibers or films of polyester, polyolefins, rayon or natural fibers such as cotton. In the case of non-woven materials, the fibers are generally to be joined together by binders such as polyacrylates. Preferred materials are polyester, rayon and blends thereof, polyethylene and polypropylene. Examples of liquid pervious layers are described in WO 99/57355, EP-A-1 023 883.

The liquid impervious layer (B) consists in general of a film/sheet of polyethylene or polypropylene.

The core (C), as well as the crosslinked swellable hydrogel forming polymer according to the present invention, comprises hydrophilic fiber material. By hydrophilic is meant that aqueous fluids spread quickly over the fiber.

The fiber material is usually cellulose, modified cellulose, rayon, polyester such as polyethylene terephthalate. Particular preference is given to cellulosic fibers such as chemical pulp. The fibers are generally from 1 to 200 μm and preferably from 10 to 100 μm in diameter. The fibers also have a minimum length of 1 mm.

Diaper construction and shape is common knowledge and described for example in WO 95/26209 page 66 line 34 to page 69 line 11, WO-A-03/104300, DE-A-196 04 601, EP-A-0 316 518 and EP-A-0 202 127.

To determine the quality of surface postcrosslinking, the dried hydrogel is tested by test methods described hereinbelow:

Methods:

Centrifuge Retention Capacity (CRC)

This method measures the free swellability of the water absorbing polymer in a teabag.

To determine the CRC 0.2000±0.0050 g of dried polymer are weighed in a teabag 60×85 mm in size, which is subsequently filled. The teabag is placed for 30 minutes in an excess of 0.9% by weight sodium chloride solution (at least 0.83 l of sodium chloride solution/1 g of polymer powder). The teabag is subsequently centrifuged at 250 G for 3 minutes. The amount of liquid retained by the hydrogel is determined by weighing back the centrifuged teabag.

Centrifuge retention capacity can also be determined by the centrifuge retention capacity test method No. 441.2-02 recommended by EDANA (European Disposables and Nonwovens Association).

Absorbency Under Load (AUL) 0.7 psi (4830 Pa)

The measuring cell for determining the AUL 0.7 psi value is a Plexiglas cylinder 60 mm in internal diameter and 50 mm in height. Adhesively attached to its underside is a stainless steel sieve bottom having a mesh size of 36 μm. The measuring cell further includes a plastic plate having a diameter of 59 mm and a weight which can be placed in the measuring cell together with the plastic plate. The plastic plate and the weight together weigh 1344 g. AUL 0.7 psi is determined by determining the weight of the empty Plexiglas cylinder and of the plastic plate and recording it as $W_0$. Then 0.900±0.005 g of dried polymer is weighed into the Plexiglas cylinder and distributed very uniformly over the stainless steel sieve bottom. The plastic plate is then carefully placed in the Plexiglas cylinder, the entire unit is weighed and the weight is recorded as $W_a$. The weight is then placed on the plastic plate in the Plexiglas cylinder.

A ceramic filter plate 120 mm in diameter and 10 mm in height and 0 in porosity is then placed in the middle of a Petri dish 200 mm in diameter and 30 mm in height and sufficient 0.9% by weight sodium chloride solution is introduced for the surface of the liquid to be level with the filter plate surface without the surface of the filter plate being wetted. A round filter paper 90 mm in diameter and <20 μm in pore size (S&S 589 Schwarzband from Schleicher & Schüll) is subsequently placed on the ceramic plate. The Plexiglas cylinder holding water absorbing polymer is then placed with plastic plate and weight on top of the filter paper and left there for 60 minutes. At the end of this period, the complete unit is taken out of the Petri dish from the filter paper and then the weight is removed from the Plexiglas cylinder. The Plexiglas cylinder holding swollen hydrogel is weighed out together with the plastic plate and the weight is recorded as $W_b$.

Absorbency under load (AUL) is calculated as follows:

$$AUL 0.7\ psi[g/g]=[W_b-W_a]/[W_a-W_0]$$

The absorbency under load can also be determined by the absorption under pressure test method No. 442.2-02 recommended by EDANA (European Disposables and Nonwovens Association).

Absorbency Under Load (AUL) 0.3 psi (2070 Pa)

The measurement is carried out similarly to AUL 0.3 psi. The weight of the plastic plate and the weight are together 576 g.

16 h Extractables

The level of extractable constituents in the water absorbing polymer can be determined by the determination of extractable polymer content by potentiometric titration test method No. 470.2-02 recommended by EDANA (European Disposables and Nonwovens Association).

Surface Tension of Aqueous Extract 0.50 g of dried polymer is weighed into a small glass beaker and mixed with 40 ml of 0.9% by weight sodium chloride solution. The contents of the glass beaker are stirred with a magnetic stirrer bar at 500 rpm for 3 minutes and are then allowed to settle for 2 minutes. Finally, the surface tension of the aqueous supernatant is measured with a K10-ST digital tensiometer or a comparable instrument comprising a platinum plate (from Kruess).

Residual Monomers

The level of unconverted ethylenically unsaturated monomers in the water absorbing polymer can be determined by residual monomers test method No. 410.2-02 recommended by EDANA (European Disposables and Nonwovens Association).

Saline Flow Conductivity (SFC)

The saline flow conductivity of a swollen gel layer under a confining pressure of 0.3 psi (2070 Pa) is determined as described in EP-A-0 640 330 as the gel layer permeability of a swollen gel layer of superabsorbent polymer, although the apparatus described on page 19 and in FIG. 8 of the previously cited patent application was modified to the effect that the glass frit (40) is no longer used, the piston (39) is made of the same plastic material as the cylinder (37) and now contains 21 equally sized holes uniformly distributed over the entire contact surface. The procedure and also evaluation of the measurement remains unchanged compared with EP-A-0 640 330. The flow rate is recorded automatically.

The saline flow conductivity (SFC) is calculated as follows:

$$SFC[cm^3 s/g]=(F_g(t=0)\times L_0)/(d\times A\times WP),$$

where $F_g(t=0)$ is the flow rate of NaCl solution in g/s obtained from a linear regression analysis of the $F_g(t)$ data of the flow rate determinations by extrapolation to t=0; $L_0$ is the thickness of the gel layer in cm; d is the density of the NaCl solution in g/cm$^3$; A is the area of the gel layer in cm$^2$; and WP is the hydrostatic pressure above the gel layer in dyn/cm$^2$.

Color Number

The color number can be determined according to ASTM D 1209.

Odor Test

To assess the odor of the swollen water absorbing polymer, 2.0 g of dry hydrogel are weighed into a 50 ml glass beaker. 20 g of 0.9% by weight sodium chloride solution at 23° C. are then added. The glass beaker holding the swelling water absorbing polymer is sealed gastight and left to stand for 3 minutes. Thereafter, the seal is removed and the odor assessed. Each sample is examined by at least 3 judges, a separate sample being prepared for each.

EXAMPLES

Example 1

Preparation of N-(2-hydroxyethyl)oxazolidin-2-one as solution in propylene glycol 5.1 mol of propylene carbonate were provided as an initial charge at 23° C. under a nitrogen atmosphere. 5 mol of diethanolamine were added over 30 to 120 minutes with stirring, and the temperature of the reaction mixture rose. On completion of the addition the mixture was heated to 120° C. in the course of 10 to 120 minutes and left to stir at 120° C. for 12 hours. Diethanolamine was >98% converted, the solution obtained comprising 60% to 63% by weight of N-(2-hydroxyethyl)oxazolidin-2-one.

Example 2

Preparation of N-(2-hydroxyethyl)oxazolidin-2-one as solution in propylene glycol with subsequent distillation 5.1 mol of propylene carbonate were provided as an initial charge at 23° C. under a nitrogen atmosphere. 5 mol of diethanolamine were added over 30 to 120 minutes with stirring, and the temperature of the reaction mixture rose. On completion of the addition the mixture was heated to 120° C. in the course of 10 to 120 minutes and left to stir at 120° C. for 2 hours. Then a 10 to 20 mbar vacuum was applied, the temperature was raised from 120° C. to 160° C. and propylene glycol was distilled off. The N-(2-hydroxyethyl)oxazolidin-2-one obtained almost quantitatively as undistilled bottom product comprised 96 to 98% by weight of product of value and had a Hazen color number in the range from 0 to 15.

Example 3

Preparation of N-(2-hydroxyethyl)oxazolidin-2-one as solution in propylene glycol by NaOH catalysis 5.1 mol of propylene carbonate were provided as an initial charge at 23° C. under a nitrogen atmosphere. 5 mol of diethanolamine were added over 30 to 120 minutes with stirring, and the temperature of the reaction mixture rose. On completion of the addition the mixture was heated to 100° C. in the course of 10 to 120 minutes. At 100° C., 2.5 mol % of NaOH in solid form were added, and the batch was left to stir at 100° C. for 2 hours. Diethanolamine was >98% converted, the solution obtained comprising 60% to 63% by weight of N-(2-hydroxyethyl)oxazolidin-2-one. The product of value had a Hazen color number in the range from 0 to 5.

Example 4

Preparation of N-(2-hydroxyethyl)oxazolidin-2-one as solution in propylene glycol by NaOH catalysis with subsequent distillation 5.1 mol of propylene carbonate were provided as an initial charge at 23° C. under a nitrogen atmosphere. 5 mol of diethanolamine were added over 30 to 120 minutes with stirring, and the temperature of the reaction mixture rose. On completion of the addition the mixture was heated to 100° C. in the course of 10 to 120 minutes. At 100° C., 2.5 mol % of NaOH in solid form were added, and the batch was left to stir at 100° C. for 2 hours. Then a 10 to 20 mbar vacuum was applied, the temperature was raised from 100° C. to 160° C. and propylene glycol was distilled off. The N-(2-hydroxyethyl)-oxazolidin-2-one obtained almost quantitatively as undistilled bottom product comprised 96-98% by weight of product of value and had a Hazen color number in the range from 0 to 25.

Example 5

Preparation of N-(2-hydroxyethyl)oxazolidin-2-one as solution in 1,3-propanediol Example 1 was repeated using 1,3-dioxan-2-one instead of propylene carbonate. Diethanolamine conversion was >98%.

Example 6

Preparation of N-(2-hydroxyethyl)oxazolidin-2-one as solution in 1,3-propanediol by NaOH catalysis Example 3 was repeated using 1,3-dioxan-2-one instead of propylene carbonate. Diethanolamine conversion was >98%.
Examples relating to production of superabsorbents:

Example 7

Production of Base Polymer

A Lödige VT 5R-MK plowshare kneader 5 l in capacity was charged with 460 g of deionized water, 213.9 g of acrylic acid, 1924.9 g of 37.3% by weight sodium acrylate solution (100 mol % neutralized) and also 2.29 g of the crosslinker glycerol-3 EO-triacrylate (triacrylate of altogether triply ethoxylated glycerol). This initial charge was inertized by bubbling nitrogen through it for 20 minutes. This was followed by initiation at about 20° C. through addition (dilute aqueous solutions) of 2.139 g of sodium persulfate dissolved in 12.12 g of water, 0.046 g of ascorbic acid dissolved in 9.12 g of water and also 0.127 g of 30% by weight hydrogen peroxide dissolved in 1.15 g of water. After initiation, the temperature of the heating jacket was closed loop controlled to the reaction temperature in the reactor. The crumbly gel eventually obtained was then dried at 160° C. in a through air drying cabinet for about 3 hours.

The dried base polymer was ground and classified to 150-850 μm by sieving off over- and undersize.

The base polymer had the following properties:
CRC=34 g/g
AUL 0.3 psi=13 g/g
Extractables 16 h=8.1% by weight
Residual moisture content=1.9% by weight
Surface tension of aqueous extract=0.0715 N/m

Examples 8 to 14

Postcrosslinking of Base Polymer from Example 7

20 g of polymer (classified to 300-850 μm by sieving) from example 7 were introduced into a Waring laboratory mixer equipped with an attachment having blunt mixing blades. Exactly 0.80 g of the postcrosslinking solution was then gradually injected with a syringe through a hole in the lid of the mixing attachment at medium speed of rotation with stirring in order that the polymer be wetted as uniformly as possible.

The postcrosslinking solution had the composition reported in table 1. In each case the end product described in the preparation examples was used.

TABLE 1

| | Postcrosslinking solutions | | |
| --- | --- | --- | --- |
| Example | Isopropanol* | Water* | Postcrosslinking agent* |
| 8 | 1.146 | 2.674 | 0.18 (Ex. 3) |
| 9 | 1.170 | 2.730 | 0.10 (Ex. 4) |
| 10 | 1.146 | 2.674 | 0.18 (Ex. 1) |
| 11 | 1.170 | 2.730 | 0.10 (Ex. 2) |
| 12 | 1.146 | 2.674 | 0.18 (Ex. 6) |
| 13 | 1.170 | 2.730 | 0.10 (Ex. 6) |
| 14 | 1.146 | 2.674 | 0.18 (Ex. 5) |

*All amounts reported in % by weight based on polymer used.

The moist polymer was homogenized by brief stirring in the mixer and then heat treated at 175° C. on a watch glass in the through air drying cabinet for 60 minutes. This was followed by sieving through an 850 μm sieve to remove agglomerates formed.

The properties of the postcrosslinked polymer are listed in table 2.

TABLE 2

Postcrosslinked polymers

| Ex. | CRC [g/g] | AUL 0.7 [g/g] | 16 h extractables [% by weight] | SFC [$10^{-7}$ cm$^3$s/g] | Surface tension of aqueous extract [N/m] | Odor on moistening |
|---|---|---|---|---|---|---|
| 8 | 27.5 | 22.9 | 7.2 | 105 | 0.072 | slightly alcoholic |
| 9 | 27.9 | 23.0 | 7.1 | 100 | 0.072 | almost odorless |
| 10 | 27.4 | 23.1 | 6.9 | 103 | 0.072 | slightly alcoholic |
| 11 | 28.0 | 23.0 | 7.2 | 107 | 0.072 | almost odorless |
| 12 | 26.6 | 22.0 | 7.3 | 113 | 0.072 | very slight |
| 13 | 27.0 | 22.7 | 7.3 | 114 | 0.073 | very slight |
| 14 | 26.8 | 22.2 | 7.0 | 110 | 0.072 | very slight |

*All amounts reported in % by weight based on polymer used.

We claim:

1. A process for postcrosslinking a water absorbing polymer comprising:
   (a) reacting respectively an aminoalcohol or a diamine with a cyclic carbonate to free an n,m diol from the cyclic carbonate and provide at least one crude postcrosslinker comprising i) a cyclic carbamate having a hydroxyalkyl group on a nitrogen atom and the n,m diol, wherein a molar ratio of the n,m diol to the carbamate is in a range of 1.1:1 to 1:2.5, or ii) a cyclic urea optionally having a hydroxyalkyl group on a nitrogen atom and the n,m diol, wherein for i) and ii), m>n and m−n>1;
   (b) treating the water absorbing polymer with the at least one crude postcrosslinker of step (a); and
   (c) optionally raising a temperature of the treated water absorbing polymer during or after step (b) to postcrosslink the water absorbing polymer.

2. The process according to claim 1 wherein the polymer treated with the at least one crude postcrosslinker is dried during step (b) or (c).

3. The process according to claim 1 wherein the crude postcrosslinker comprises the cyclic carbamate having a hydroxyalkyl group as a nitrogen atom and the n,m diol.

4. The process according to claim 1 wherein the crude postcrosslinker further comprises a cyclic carbonate.

5. The process according to claim 1 wherein a basic catalyst is used in the reaction of the aminoalcohol with the cyclic carbonate.

6. The process according to claim 5 wherein the basic catalyst is sodium hydroxide.

* * * * *